(12) United States Patent
Desire

(10) Patent No.: US 6,398,922 B2
(45) Date of Patent: Jun. 4, 2002

(54) PHOTOCHEMICAL GAS-LIQUID PROCESS FOR HALOGENATING ALKYLBENZENES

(75) Inventor: Gerard Desire, Lens (FR)

(73) Assignee: Elf Atochem S.A., Puteaux (FR)

( * ) Notice: Subject to any disclaimer, the term of this patent is extended or adjusted under 35 U.S.C. 154(b) by 0 days.

(21) Appl. No.: 09/785,317

(22) Filed: Feb. 20, 2001

Related U.S. Application Data

(63) Continuation of application No. 08/186,564, filed on Jan. 26, 1994, now abandoned.

(30) Foreign Application Priority Data

Jan. 28, 1993 (FR) .............................. 93 00863

(51) Int. Cl.⁷ .............................................. C07C 17/00
(52) U.S. Cl. .............................. 204/157.94; 204/157.6; 204/157.65; 204/157.99; 204/158.1; 422/186.3
(58) Field of Search .................. 204/157.6, 157.65, 204/157.94, 157.99, 158.1; 422/186.3

(56) References Cited

U.S. PATENT DOCUMENTS

| 3,816,287 A | 6/1974 | Bockmann et al. |
| 3,993,911 A | 11/1976 | Graentzel |
| 4,056,455 A | 11/1977 | Lademann et al. |
| 4,141,830 A | 2/1979 | Last |
| 4,189,363 A | 2/1980 | Beitzel |
| 4,331,821 A | 5/1982 | Schubart et al. |
| 4,348,265 A | 9/1982 | Ström |
| 4,452,678 A | 6/1984 | Olliver |

FOREIGN PATENT DOCUMENTS

| EP | 0 111 253 | 6/1984 |
| GB | 928 693 | 5/1960 |
| GB | 1 084 212 | 9/1967 |
| JP | 61/187930 | 8/1986 |

OTHER PUBLICATIONS

Ullmanns Encyklopadie Der Technischen Chemie; "Reaktionsapparate für GAS–Flüssing–Reaktionen" (1973/p. 372).

Chemisch–Technisches LexiKon ; von Dieter Osteroth (1979, pp. 209–210).

Primary Examiner—Dwyane O. Jones
Assistant Examiner—C. Delacroix-Muirheid
(74) Attorney, Agent, or Firm—Burns, Doane, Swecker & Mathis, L.L.P.

(57) ABSTRACT

The invention provides a process for carrying out a photochemical gas-liquid process for halogenating alkylbenzenes, the process being carried out in a photochemical gas-liquid reactor comprising a vessel, a central source of radiation, a gas distributor, and additionally, inner sleeve means arranged concentrically between the source of radiation and the vessel, the inner sleeve means providing for internal recirculation of reaction liquid.

17 Claims, 3 Drawing Sheets

US 6,398,922 B2

PHOTOCHEMICAL GAS-LIQUID PROCESS FOR HALOGENATING ALKYLBENZENES

This application is a continuation of application Ser. No. 08/186,564, filed Jan. 26, 1994, now abandoned.

FIELD OF THE INVENTION

The present invention relates to a novel photochemical gas-liquid process for halogenating alkylbenzenes, particularly a process for chlorination of toluene.

BACKGROUND OF THE INVENTION

Photochemical chlorination, or in broader terms halogenation, of hydrocarbon derivatives is currently employed on a wide scale. Nevertheless, in reactions involving substituting hydrogen atoms by chlorine atoms, numerous problems of selectivity occur. One representative example of photochemical chlorination is the chlorination of alkylbenzene, particularly toluene.

Photochemical chlorination of toluene principally leads to the formation of benzyl chloride, benzylidene chloride and phenylchloroform.

It is also known that apart from this principal chlorination of the methyl group of the toluene molecule, unwanted small amounts of chlorinated derivatives on the aromatic ring always form, particularly chlorotoluenes and homologous compounds thereof: benzyl chloro-chlorides, benzylidene chloro-chlorides and chlorophenylchloroforms.

It is moreover known that the proportion of chlorine derivatives on the aromatic ring increases substantially as the degree of chlorination of the mixture increases. Starting from 0.1 to 0.5%, when limited to benzyl chloride, the proportion of chlorine derivatives on the aromatic ring can reach or even exceed 5% when it is desired to achieve complete chlorination of the methyl group, for the purposes of producing essentially phenylchloroform.

For this reason, it is difficult to obtain high-purity phenylchloroform by direct chlorination without having recourse to distillation of the reaction mixture. Certain patents hence consider carrying out incomplete chlorination in order to limit the formation of derivatives, and to then subsequently distil the mixtures obtained with a subsequent increase in cost price.

Numerous photochemical reactors have been developed, some of them for a specific use. Thus JP-A-85 25153 discloses a benzene chlorination reactor, but this chlorination reaction does not involve in any critical way the problems of selectivity listed above for toluene. This reactor is a special reactor, having fluid convection. The vertical cylindrical reaction vessel has an internal cylindrical wall with a mirror surface. An internal fluid circulation is achieved by means of a rising flow inside the cylinder, and a descending flow between the outer casing of said cylindrical wall and the said internal wall. The reaction vessel is fed with gas from the bottom, and the light source is disposed inside the reactor.

The documents "Reaktionsapparate für Gas-Flüssig-Reaktionen", p. 372, and "Chemischtechnisches Lexikon" describe reactors of the type convection reactor using the air-lift principle and/or which include an entraining flow which is injected at the base of the apparatus. The example of implementation concerns oxidation of n-butane.

None of these documents discloses the process according to the present invention.

SUMMARY OF THE INVENTION

The present invention provides a photochemical gas-liquid process for halogenating alkylbenzenes enabling high yield and high selectivity to be achieved together with other advantages.

DETAILED DESCRIPTION OF THE INVENTION

Figure 1:
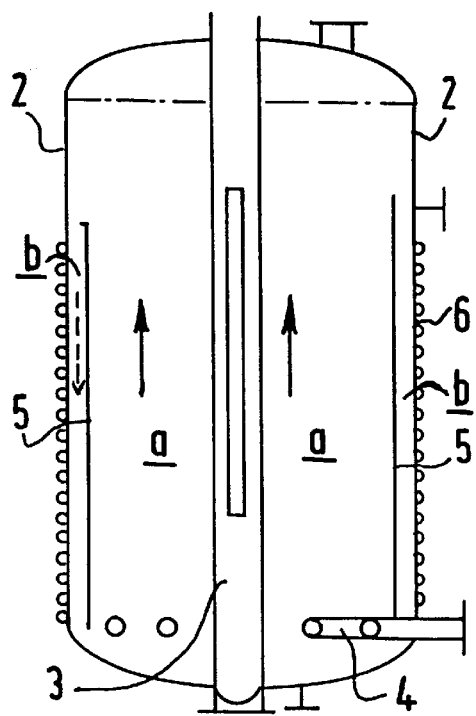
FIG. 1 is a general view of a reactor for carrying out the process according to the invention.

The present invention provides a process for halogenating alkylbenzenes which is carried out in an axially symmetric photochemical gas/liquid reactor, comprising:
a vessel;
a central source of radiation;
at least one gas distributor, at the bottom of said reactor;
inner sleeve means arranged concentrically between the source of radiation and the vessel, said inner sleeve means allowing internal recirculation of reaction liquid, said recirculation comprising a rising movement in the space located between the source and the inner sleeve means and a descending movement in the space situated between the vessel and the inner sleeve means.

The present process is particularly useful for chlorinating toluene. This process allows a selectivity towards benzyl chloride or benzylidene chloride or phenylchloroform, depending upon the desired product.

This reactor for carrying out the process enables three concentric zones to be defined inside the reactor:
a central zone where the source of radiation is provided;
an annular reaction zone disposed around the central zone and including, at its lower portion, a gas distribution system with calibrated orifices making it possible to impose a certain size on the gas bubbles. The originality of the reaction zone, i.e. the area between the source and the inner sleeve means, lies in the controlled rising recirculation of the liquid therein, along the source;
a peripheral zone in which there is controlled descending circulation of liquid that has undergone exchange in the reaction zone. This zone further provides the heat exchange necessary to maintain suitable temperatures via heat exchange surfaces (with heating, or more frequently cooling, provided on the outer wall of the reactor).

Reactors for carrying out the present process also enable the following aims to be met:
the cross-section of the reaction zone of an internal-recirculation reactor is some three times smaller than that of a conventional reactor, without recirculation, for the same gas flow rate;
a two to three-fold reduction in the height of liquid through which the gas needs to pass in order to achieve the same degree of chlorine or halogen fixation;

recirculation of liquid along the source of radiation enables the latter to be used much more efficiently. The number and power of the lamps can be reduced, and they can all be housed in a single central tube, even for high-capacity reactors;

the presence of the inner sleeve means close to the reactor wall enables a considerable, up to threefold, increase in overall heat exchange coefficient. This increase in exchange coefficient is particularly useful when designing large-capacity reactors;

the combination of the above advantages enables reactors to be designed which are much smaller and compact when compared to conventional reactors of equivalent production capacity, or individual production capacities to be obtained which are well above those obtainable in conventional reactors not employing recirculation.

In one embodiment, the inner sleeve means extends down to the level of the distributor or down to an intermediate level situated between the distributor and the bottom of the vessel.

In another embodiment, the inner sleeve means extend down to the bottom of the vessel and includes a series of orifices located at an intermediate level between the distributor and the bottom of the vessel Regarding the inner sleeve means, this can have any form provided it fulfils the recirculation function. Its shape can notably be a scaled-down version of the reactor wall. Viewed in cross-section, it can have a straight section or segment, at the upper or lower, or both, ends of which one or more other segments or curved sections making an angle with the straight segment can be present. The inner sleeve means can also be subdivided into sub-sections, either arranged horizontally in line thus forming calibrated sleeve means or alternately offset with respect to each other, in other words when viewed in cross-section, the sub-sections are arranged in line but making an angle with the general direction of the sleeve member. The sleeve means can also consist of sub-sections arranged generally vertically but with gaps of varying dimensions between them. They can also be offset from each other in the radial direction of the reactor. Last, it should be noted that this inner sleeve means can also be mirror-like so as to reflect inwards the radiation emitted by the source.

Thus any arrangement of the inner sleeve means is possible, provided it is able to fulfil the recirculation function. Thus, the inner sleeve means should be considered in this invention to mean any means capable of ensuring internal liquid recirculation.

In one embodiment, the inner sleeve means includes slots of a calibrated size along part or all of its length.

Internal recirculation, which is a feature of the reactor for carrying out the process according to the invention, preferably starts at a point below the distributor, in the vicinity of the bottom of the vessel, the liquid flow thus passing through the space defined by the distributor.

The central radiation source can be arranged in several alternative ways inside the reactor.

In one embodiment, the source extends right through the reactor from one end to the other.

In another embodiment, the source passes through the reactor cover only.

The central source preferably consists of one or several transparent tube(s) arranged in axial symmetry, a single tube being employed advantageously.

Any suitable gas distributor can be employed, such as a grid, concentrically perforated toroidal members or any other embodiment readily accessible to the person skilled in the art.

Preferably, the distributor(s) consist(s) of one or several concentric toroidal members provided with calibrated holes in their upper halves.

In one embodiment, the reactor comprises one single distributor at the bottom of the reactor.

In another embodiment, the reactor comprises at least two distributors, situated at different levels inside said reactor.

The operating conditions of the reactor as regards temperature, pressure and so on are those conventionally employed for the particular reaction.

Preferably, the velocity of the liquid in the rising movement occurring in the space situated between said source and said inner sleeve member is comprised between 0.1 and 0.8 m/s and preferably between 0.25 and 0.60 m/s.

With the liquid velocity designated as U and the velocity of the gas with respect to the velocity of the liquid designated by V, the velocity of the gas relative to the reactor is U+V. In one embodiment, the velocity of the gas U+V is comprised between 0.3 and 1.1 m/s.

Preferably, the velocity of the liquid in the descending movement situated in the space between said inner sleeve means and said vessel is comprised between 0.5 and 3 m/s, preferably between 1 and 2.5 m/s.

Preferably, the fraction of the volume occupied by the gaseous phase represents 10 to 50%, preferably 20 to 40% by volume, of the volume of the vessel defined between the source and the inner sleeve means.

Preferably, the diameter of the bubbles generated by the distributor is comprised between 3 and 15 mm, preferably 6 and 10 mm.

The reactor for carrying out the process of the present invention, is one having axial symmetry, and is preferably a body of revolution. It can be cylindrical or cylindroconical.

The reactor and its implementation for carrying out the process of the invention will now be described in detail, with reference to the figures of the drawing.

FIG. 1 shows a general view of a reactor for carrying out the process according to the present invention. Reactor 1 comprises several individual parts manufactured from materials that are appropriate to the chemical reaction considered. For example, for the chlorination of toluene, the parts of the reactor are manufactured from non-ferrous alloys, for example nickel or alloys thereof. Reactor 1 comprises a vessel 2, a central source of radiation 3 which conventionally is a transparent tube, and a distributor 4. The dimensions of the reactor, defined by its vessel, are typically: length: 1 to 4 m, advantageously 1.5 to 3 m, diameter: 0.5 to 2 m, advantageously 0.7 to 1.5 m. The transparent tube or tubes are generally in pyrex glass or quartz, or in any other material which is transparent within the range covering the radiation wavelength employed. Conventionally, the wavelength corresponds to the ultraviolet (U.V.) part of the spectrum. This tube can be made of a material that is transparent to the wavelength employed, for example U.V., and which is substantially opaque to other wavelengths in order to limit the formation of by-products or the breakdown of the desired products, which could possibly happen at wavelength different from the working wavelength. This result is achieved for example with pyrex glass which is transparent to U.V., in other words a radiation of about 250 to 400 nm wavelength, but which is substantially opaque to radiation below 200 nm. The number of lamps and their power vary with the desired production capacity. The number of lamps is generally comprised between 1 and 10, and most frequently between 2 and 4, one lamp being however one of the preferred embodiments. Their individual power varies between 0.1 kW and 20 kW, most frequently between 0.2 and 4 kW. The individual power of the lamps varies between 0.1 kW and 20 kW, most frequently between 0.2 and 4 kW. These lamps can be arranged around a central rod which acts as a support, or be disposed within several tubes. Thus, it is possible to employ either a dual-lamp central light source or 3 single-lamp light sources, account should be taken of the influence of how the light sources are arranged on the hydraulic flow inside the reactor. Depending on the dimensions of the tube, the lamps can be at the same level or on different levels. The tube or tubes have quite conventional dimensions and their length substantially corresponds to the length of the reactor. Actually, the tube length is such that the tube or tubes are substantially completely immersed in the reaction fluid. The diameter of the central tube, when only one tube is employed, is conventionally comprised between 50 and 500 mm, advantageously 100 to 200 mm. The reactor moreover comprises, according to the invention, inner sleeve means 5 providing recirculation. Thus, the cylindrical or cylindricoconical reactor arranged in correspondence to the present invention comprises, moving from the axis towards the periphery:

a central transparent tube designed to house the radiation source;

an annular reaction zone (a) around the central transparent tube;

a peripheral zone (b) around the reaction zone, the purpose of which is to ensure recirculation of the fluid from the reaction zone, and to facilitate heat exchange.

In zone (a), the direction of recirculation is indicated by the solid arrow whereas the direction of circulation in zone (b) is indicated by the dashed arrow as shown in FIG. 1. At the upper portion of the reaction zone, the entrained fluid overflows into the peripheral recycling and heat exchange zone, whereas the gas consisting of gas introduced that has not reacted and, possibly, gas produced by the reaction is evacuated from the top portion of the reactor. Nevertheless, the gas that has not reacted is frequently negligible in view of the efficiency of the reactors described here. For example, the flow of unfixed chlorine becomes negligible at the end of chlorination, during chlorination of the substituting methyl group on the aromatic ring. One can in fact consider that the gas flow is for the major part made up by gas introduced and vaporised organic compounds, regardless of the rate of fixation of the gas. The reactor also comprises an outer jacket 6 of the double-wall type preferably in the form of half-shells, ensuring heat exchange. The existence of the inner sleeve means or intermediate wall enables a significant increase in heat exchange coefficients to be obtained, thus significantly reducing the surface area required for heat exchange, when compared to the-areas needed in a conventional reactor without internal recirculation.

Figure 2:
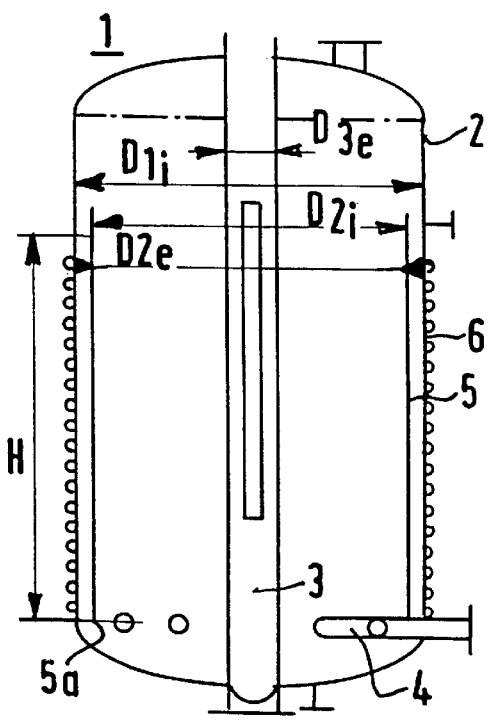
FIG. 2 is a diagrammatical view illustrating one embodiment of a reactor for carrying out the process of the, invention.
Figure 3:
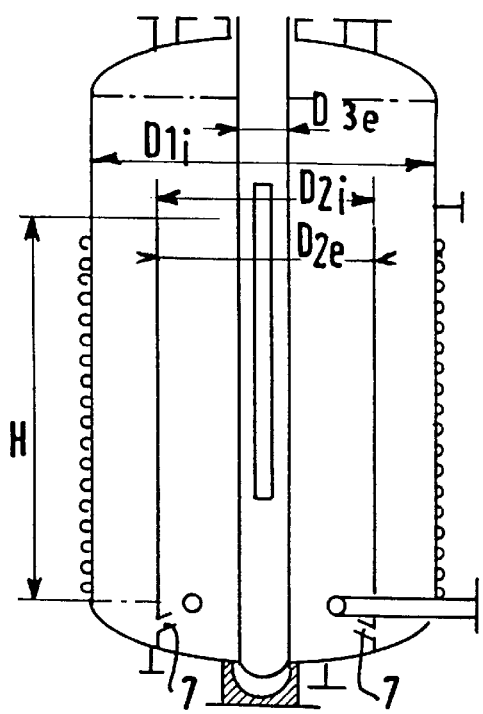
FIG. 3 is a diagrammatical view showing a second embodiment of a reactor for carrying out the present process.

The inner sleeve means 5 can be located inside the reactor according to several possible dispositions. FIGS. 2 and 3 give two embodiments.

FIG. 2 shows an embodiment in which the intermediate inner sleeve means stops at distributor level, or at a level between the distributor and the bottom of the reactor.

The reference numerals are the same as those used in FIG. 1. The fluid flows freely towards the reaction zone below the gas distributor or distributors. Surface S' is the surface area defined by the inside diameter of the vessel, $D_{1i}$, and by the outer diameter of the inner sleeve means $D_{2e}$, giving:

$$S' = \frac{\pi}{4}(D_{1i}^2 - D_{2e}^2)$$

It is surface area S' which determines the recirculation velocity and flow rate and consequently the velocity of flow in the reaction zone having a surface area of S. The surface area S is defined by the inside diameter of the inner sleeve means $D_{2i}$ and the outer diameter of the transparent tube $D_{3e}$, giving:

$$S = \frac{\pi}{4}(D_{2i}^2 - D_{3e}^2)$$

The section S' is calculated so that the specified velocity of the fluid in the reaction zone is comprised between 0.1 and 0.8 m.s$^{-1}$, and that the fraction of the volume occupied by the gas represents 10 to 50%, preferably 20 to 40% of the volume of the reaction zone. The velocity of flow in the recirculation zone between the inner sleeve means and the vessel is then generally comprised between 1 and 3 m.s$^{-1}$. This embodiment, where the inner sleeve means stops at distributor level, or at a level comprised between the distributor and the bottom of the reactor, is recommended but is not limited to the case where reaction kinetics are fast and requires efficient heat exchange, rendered possible by the high velocity of the fluid in the reaction zone. FIG. 2 shows the specific embodiment in which the inner sleeve means stops at distributor level, on FIG. 5a.

FIG. 3 shows another embodiment in which the inner sleeve means extends down to the bottom of the reactor. Orifices 7 are provided at the lower portion of the intermediate inner sleeve means. Preferably their outlet is oriented towards the gas distributor so as to ensure permanent renewal of fluid at this level. This orientation is shown on FIG. 3. These orifices may be jets, circular holes, rectangular slots, or of other types. The number and cross-sectional area of these orifices are determined so as to adjust the fluid flow rate/gas flow rate ratio to the selected value. Adjustment of this ratio enables the velocity of flow in the reaction zone to be varied. In this embodiment, the surface area S' or section of the recirculation peripheral zone no longer determines the fluid flow rate, and can be increased at will. This configuration is recommended for reactions having a relatively slow reaction rate and where it is desired to preserve a sufficient mass of liquid in the peripheral zone for operational stability, but is not limited to such-reactions. Operating conditions, regarding velocity of flow and the fraction of the volume occupied by the gaseous phase are similar to those in the previous embodiment.

Figure 4:
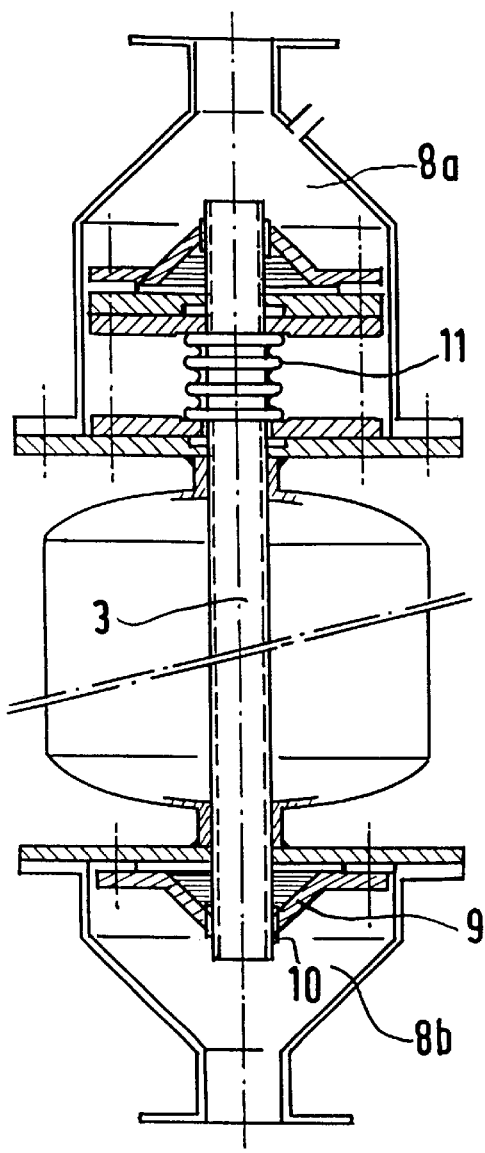
FIG. 4 shows an alternative embodiment of the reactor for carrying out the present process.

FIG. 4 shows an embodiment in which the tube constituting the source of radiation passes right through the reactor, the tube then being open at both ends. It can pass through the central end pipe fittings of the cover and base, 8a and 8b respectively of the reactor when such end pipe fittings are present. These end pipe fittings, for introducing gas at the bottom and drawing it off at the top of the reactor can obviously also be provided laterally just like in any other of the embodiments according to the present invention. A retaining grid 9 rigidly fixed to the bottom end fitting of the reactor prevents the tube from changing position, and simultaneously acts as a support for a central rod designed to support the lamps. Sealing at the bottom of the reactor is provided by a sliding assembly comprising, notably, an annular seal 10 generally in PTFE or any other material, which is resistant to the reaction medium and a clamping arrangement for the annular seal mounted on a non-rigid support. Sealing at cover level of the reactor is obtained using the same principle but with the addition of an expansion concertina arrangement 11 designed to compensate variation in expansion between the transparent tube and the reactor. The tube end fittings at the cover and bottom of the reactor are connected to a circuit so that, in the unlikely case that the transparent tube breaks, there can be no danger of a breakdown of confinement and escape to the outer medium.

The opening in the transparent tube at the two ends thereof allows regulated and pressurized circulation of inert gas inside the transparent tube.

Figure 5:
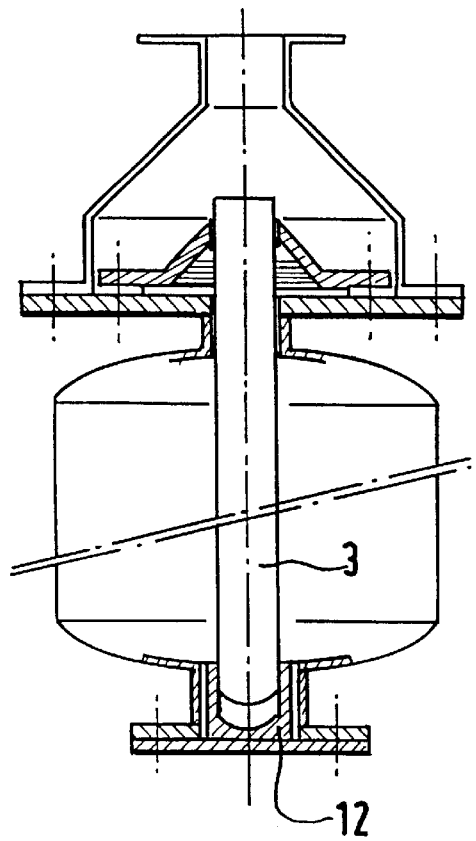
FIG. 5 shows another embodiment of the reactor for carrying out the present process.

FIG. 5 shows an embodiment in which the tube only passes through the cover. In this case, the tube is blind, in other words is closed at its lower portion. The lower rounded end of the tube rests on a stopper 12, preferably of PTFE, placed in the tube end fitting at the bottom of the reactor. The hollow shape of the stopper allows the transparent tube to slide sufficiently to absorb variations in expansion between the transparent tube and the reactor. The need to fit the concertina arrangement counteracting expansion at the reactor cover level then becomes superfluous.

Figure 6A:
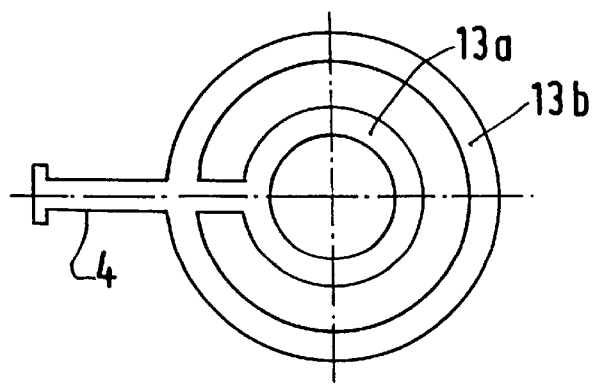
FIGS. 6A and 6B show a distributor.
Figure 6B:
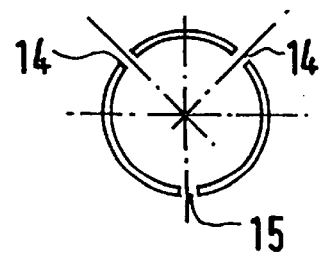

FIGS. 6a and 6b are a sectional view of a distributor according to one embodiment of the invention, FIG. 6a showing a distributor and FIG. 6b being a cross-sectional view thereof. This distributor consists of one or several concentric rings 13a and 13badapted to the size of the reactor and carrying holes 14 scaled up to specific dimensions generally comprised between 3 and 15 mm and, most frequently, between 6 and 10 mm. A free space is left between the rings, representing from 40 to 80% of the cross-section of the reaction zone and this is designed to allow the recycled liquid to flow below the distributor.

As indicated in FIG. 6b, the calibrated holes are generally arranged on the upper half of the ring in two rows separated by a central angle which can vary but is most frequently comprised between 60 and 180° and, preferably, 90 to 135° to facilitate gas bubble entrainment in the flow of recirculation fluid. Several smaller holes 15 are also provided at the bottom portion to ensure fluid can flow out when the reactor is shut down, and then started up. The bubbles of gas introduced entrain recycled fluid at a determined velocity and according to a well defined gas phase/fluid phase ration which is optimized in order to obtain the best reaction kinetic. Generally, the reactor is dimensioned so as to obtain a velocity of fluid circulation comprised between 0.1 and 0.8 m/s, preferably 0.25 and 0.60 m/s and the gaseous phase constituting from 10 to 50%, preferably 20 to 40% of the volume of the reaction zone.

Figure 7:
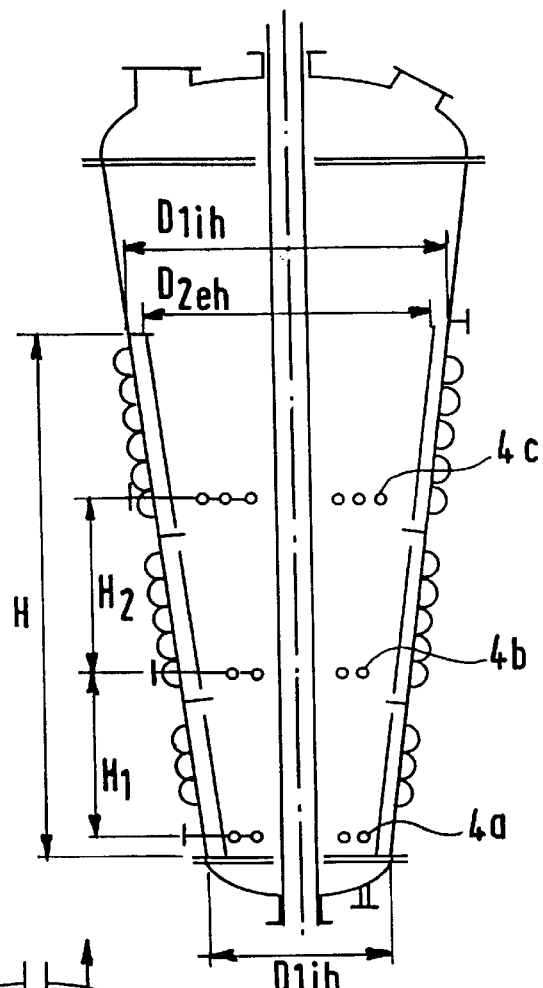
FIG. 7 shows a further embodiment of a reactor for carrying out the process according to the present invention.

FIG. 7 shows one alternative embodiment of the present invention in which several distributors are present and in which the reactor has a cylindro-conical shape. Three distribution levels, 4a, 4b and 4c are shown in this figure at levels O, $H_1$ and $H_2$. H is the total height of the reaction zone. Moreover, the dimensions of the cylindro-conical reactor are given by $D_1$ib which is the inside diameter at the bottom of the vessel, $D_1$ih, the inner diameter at the top part of the vessel, and $D_2$eh is the outside diameter of the inner sleeve means at the top thereof. Here, the gas flow from the lower distributors gets added to the flow from the upper distributors. Thus, the reactor is provided with this particular shape so as to substantially maintain the same flow parameters at all levels in the reactor.

Figure 8:
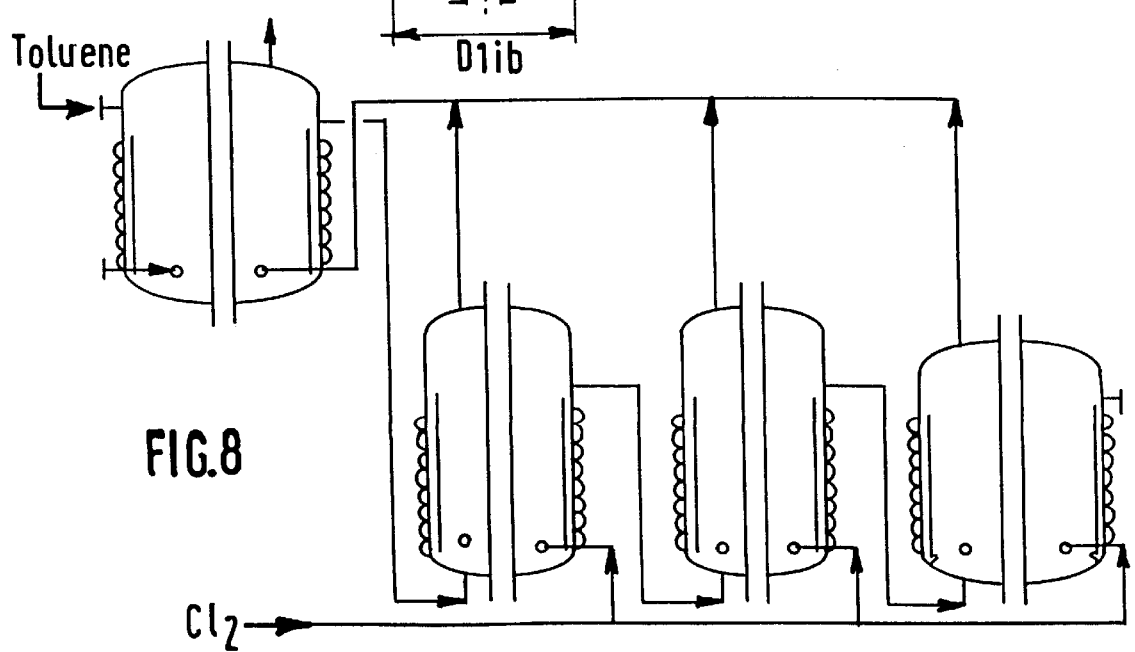
FIG. 8 shows an example of a plant or production line comprising several reactors.

FIG. 8 is a diagrammatical representation of an installation comprising several reactors according to the invention. The mode of operation of the plant is detailed in example 2.

Figure 9:
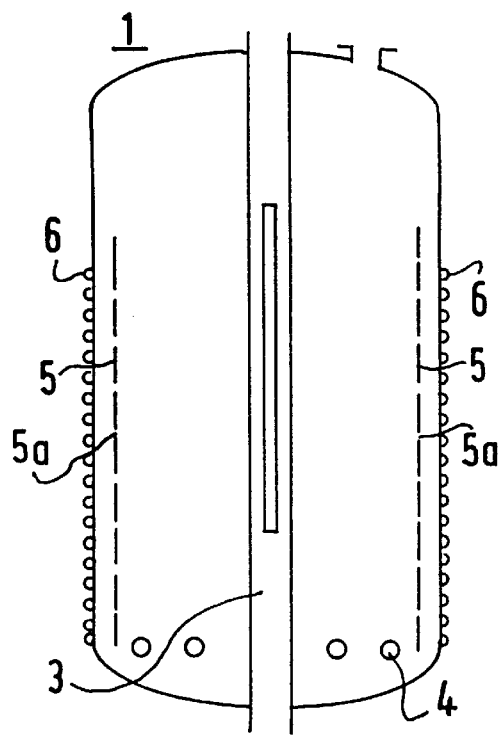
FIG. 9 shows a further embodiment of the invention.

FIG. 9 shows another alternative embodiment of a reactor in which the inner ring member is a plate provided with calibrated slots 5a. These slots may be present on only a part of the tubular member. This enables recirculation to be primed and maintained regardless of the level to which the reactor is filled. The other reference numerals are identical to those employed in FIGS. 1 to 3.

The invention thus provides a halogenation process carried out in the above-described reactor. The following are examples which should not be considered as limiting, of typical reactions:

aromatic hydrocarbon side chain chlorination:
   methylbenzene (toluene, xylenes, tri- and polymethylbenzenes);
   other alkylbenzenes; in this case it is chlorination of a carbon atom next to the aromatic ring which is obtained preferably,
   polycyclic aromatic hydrocarbons (methylnaphthalenes, for example)

aliphatic hydrocarbon chlorination;

other halogenations;

generally speaking:
   all gas-liquid alkylbenzene halogenation reactions in which significant gains in reaction kinetics and selectivity are required thanks to the implementation of optimized recirculation for the liquid velocity in the reaction zone, the volume fraction of gas in the reaction zone, diameter of the bubbles, and recirculation. Such reactors can thus implement any gas-liquid reaction by a suitable choice of optimal values associated with the three parameters above: velocity/fraction/diameter, recirculation being either internal or external with the provision of a recirculation loop.

Reactors used with these processes can be employed singly or coupled, for example in series, with other reactors which may be conventional or in accordance with the present invention.

Thus, it is possible to couple an external heat exchanger with recirculation means onto the reactors described. The exchanger can receive part or all the recirculating fluid in the reactor.

The general principles described also allow current reactors to be modified so that they can be transformed with advantage, through the incorporation of an intermediate tubular member.

The chlorination reaction of toluene can be mentioned by way of example, in which three desired products can be obtained, benzyl chloride (monosubstitution), benzylidene chloride (disubstitution) and phenylchloroform (trisubstitution or complete substitution).

When it is desired to essentially produce benzyl chloride, in other words in a benzylidene/benzyl chloride ratio <0.15, a single reactor will generally be used. An incomplete chlorination can be carried out in order to obtain a mixture at the outlet from the reactor containing on average:

| | |
|---|---|
| toluene | 50 to 40% |
| benzyl chloride | 46 to 53% |
| benzylidene chloride | 2 to 7% |

Several smaller reactors can also be connected in series enabling a smaller proportion of benzylidene chloride to be obtained, which may proof to be advantageous.

When it is desired to produce benzylidene chloride, one can operate as follows. Gaseous effluent from the second reactor is recycled back to the first reactor so as to rid it of the last residual amounts of unfixed chlorine.

When it is desired to produce phenylchloroform, it is generally preferable to operate with several reactors in series. Two to six reactors in series are employed or even more, 3 to 5 reactors being advantageous. FIG. 8 illustrates an example of a plant or production line for phenylchloroform. The first reactor is fed with toluene. The necessary chlorine is distributed by means of a multi-stage feed, in a calculated manner between the various reactors so as to ensure regular progression of chlorination from the first up to the last reactor. The first reactor is moreover supplied with the gaseous effluent from the reactors that follow it so as to recycle unfixed chlorine originating from the intermediate reactions, and the final reaction, implemented in the remainder of the reactors. This plant enables phenylchloroform in a 98% guaranteed content to be obtained at the outlet from the last reactor. Moreover, this plant allows mixtures rich in benzylchloride and/or benzylidene chloride to be drawn off at other stages, and particularly at the first stage. After distillation of these mixtures, benzyl chloride or benzylidene chloride of high purity can be obtained. The reactor of the present invention furthermore makes it possible to reduce the number of reactors in series in a production line, notably one producing phenylchloroform.

It is thus possible, thanks to the advantages reactors implementing the process provide, to obtain production capacities of 20 to 25000 metric tons/year, expressed of fixed chlorine, either from a single reactor if benzyl chloride is concerned or from a scaled-down production line if phenyl-chloroform is concerned. Moreover, the increase in chlorination velocity of the lateral chain of toluene and the corresponding reduction in residence time, notably of the liquid phase, are achieved to the detriment of chlorination of the ring, said chlorination being reduced to unobtainable limits when conventional reactors are employed. It is thus possible to obtain benzyl chloride containing less than 500 ppm of chloro-toluene, as well as phenylchloroform having purity higher than 98% at the output from the reactor. This makes it possible to dispense with costly distillation of these products.

The advantages highlighted in the case of chlorination of toluene are not specific to this particular reaction: they are a general feature of two-phase gas/liquid photochemical reactions.

The following examples illustrate the invention without limiting it.

EXAMPLE 1

Production of benzyl chloride

A cylindro-conical reactor having three injection levels as shown in FIG. 7 was employed. The dimensions of this reactor, with reference to FIG. 7 were:

| | |
|---|---|
| $D_1ih$ | 1.35 m |
| $H_1$ | 0.75 m |
| $D_2ib$ | 0.75 m |
| $H_2$ | 0.75 m |
| $D_1ih–D_2eh$ | 44 mm |

The reaction was carried out under the following operating conditions:

| | |
|---|---|
| liquid velocity in the reaction zone | $0.39 \ m \cdot s^{-1}$ |
| liquid velocity in the recirculation zone | $1.82 \ m \cdot s^{-1}$ |
| gas velocity in the reaction zone | $0.61 \ m \cdot s^{-1}$ |
| volume percentage of gas phase | 28% |
| temperature (T) | 95° C. |
| pressure (P) | 760 Torr (0.1 MPa) |
| total gas flow at above T and P ($Cl_2$ + HCl + vaporized organic compounds) | $0.184 \ m3 \cdot s^{-1}$ |
| chlorine flow rate | $900 \ kg \cdot h^{-1}$ |

The normal operating running conditions were established and the following results were obtained, on the basis of a duration of production of 3 days, after distillation of the mixture leaving the reactor:

| | Amount (3 days) | Purity | chloro-toluene content |
|---|---|---|---|
| benzyl chloride | 99.6 tons | 99.85 | <500 ppm |
| benzylidene chloride | 9.5 tons | | |

EXAMPLE 2

Production of phenylchloroform

A series of reactors having the following dimensions, with reference to FIG. 2 (the inner sleeve means stopping at an intermediate level between the single distributor and the bottom of the reactor):

| | |
|---|---|
| $D_{1i}$ | 0.99 m |
| $D_{2e}$ | 0.91 m |
| $D_{2e}$ | 0.904 m |
| $D_{3e}$ | 0.125 m |
| H | 0.9 m |

These reactors were connected in the arrangement shown in FIG. 8. The complete installation consisted of three continuous reactors (1, 2, 3) connected in series and a final discontinuous stage made up by two alternating reactors (4A, 4B), one being in service at a time. The chlorine was distributed between reactors 1, 2, 3, 4A and 4B.

The operating conditions were as follows:

| | Reactor 1 | Reactor 2 | Reactor 3 |
|---|---|---|---|
| velocity U of liquid in reaction zone (m/s) | 0.55 | 0.33 | 0.30 |
| % of gas phase gas reaction zone (%) | 29 | 15 | 13 |
| velocity U + V of gas in reaction zone (m/s) | 0.9 | 0.8 | 0.8 |
| temperature (° C.) | 100 | 145 | 155 |
| pressure (Torr(MPa)) | 760 (0.1 MPA) | 850 (0.112 MPa) | 850 (0.112 MPa) |
| total gas flow rate (m3/s) | 0.16 | 0.07 | 0.05 |
| fresh chlorine flow rate (kg/h) | — | 410 | 300 |
| recovered chlorine flow rate (kg/h) | 40 | — | — |

At this stage in the chlorination, i.e. after the third reactor, the phenylchloroform content exceeded 90%, in other words the amount of chlorine fixed exceeded 95% of the total.

In this particular example, the final stage is discontinuous. The last reactor fulfils the multiple functions of regulating the end of chlorination as well as the temporary storage reservoir for supplementary analytic analyses. Its dimensions are as follows:

| | |
|---|---|
| $D_{1i}$ | 1.58 m |
| $D_{2e}$ | 1.48 m |
| H (inner inner sleeve means) | 1.5 m |
| reactor volume | 5 m3 |

As the liquid level in the last discontinuous reactor was variable, the inner sleeve means defining the recirculation zone was provided with calibrated slots in accordance with FIG. 9, enabling recirculation to be primed regardless of the level to which the discontinuous reactor was filled.

The operating conditions were as follows:

| | |
|---|---|
| Temperature (° C.) | 155 |
| Pressure Torr (MPa) | 850 (0.112 MPa) |
| Average Cl$_2$ flow rate (kg/h) | 54 |

The gaseous effluent containing the excess chlorine was recycled to reactor 1 in conformity with FIG. 8.

The following results are obtained under normal operating conditions:

Phenylchloroform:

| | |
|---|---|
| amount over 3 days | 50.03 metric tons |
| purity | 98.41% |

The last reactor can advantageously be replaced by a continuous reactor the inner sleeve means of which, defining the recirculation zone, descends down to the bottom of the reactor as in FIG. 3, the respective dimensions of which are:

| | |
|---|---|
| $D_{1i}$ | 0.4 m |
| $D_{2e}$ | 0.3 m |
| $D_{3e}$ | 0.175 m |
| H | 1.2 m. |

What is claimed is:

1. A process for halogenating alkylbenzenes in an axially symmetrical photochemical gas/liquid reactor, wherein said reactor comprises:

a vessel;

a central radiation source;

at least one gas distributor at the bottom of said reactor; and an inner sleeve means arranged concentrically between the radiation source and the vessel, said inner sleeve means comprising slots along at least a part of its length, said inner sleeve means allowing internal recirculation of reaction liquid, said recirculation comprising a rising movement of the liquid in the space situated between the radiation source and the inner sleeve means and a descending movement in the space situated between the vessel and the inner sleeve means, said process comprising:

introducing a liquid phase comprising an alkylbenzene into the vessel and a gas phase comprising a halogen into the gas distributor;

recirculating the reaction liquid within the vessel; and calibrating the size of the slots to enable recirculation to be printed and maintained regardless of the level to which the reactor is filled;

whereby a reaction product is formed which is substantially free of derivatives of alkylbenzene that are halogenated on the aromatic ring.

2. The process according to claim 1, comprising providing the liquid rising in the space situated between the radiation source and the inner sleeve means with a velocity of 0.1–0.8 ms.

3. The process according to claim 1, comprising occupying 10–50% of a volume defined between the radiation source and the inner sleeve means with the gas phase.

4. The process according to claim 1, comprising releasing bubbles of the gas phase from the distributor having a diameter of 3–15 mm.

5. The process according to claim 1, comprising starting the recirculation at a point below the distributor, in the vicinity of the bottom of said reactor.

6. The process according to claim 1, comprising providing the distributor in the form of at least one concentric toroidal member provided with holes in its upper half.

7. The process according to claim 1, comprising providing at least two distributors, situated at different levels, inside said reactor.

8. The process according to claim 1, comprising providing the liquid rising in the space situated between the radiation source and the inner sleeve means with a velocity of 0.25–0.6 m/s.

9. The process according to claim 1, comprising providing the liquid descending in the space between said inner sleeve means and said vessel with a velocity of 0.5–3 m/s.

10. The process according to claim 1, comprising providing the liquid descending in the space between said inner sleeve means and said vessel with a velocity of 1–2.5 m/s.

11. The process according to claim 1, comprising occupying 20–40% of a volume defined between the radiation source and the inner sleeve means with the gas phase.

12. The process according to claim 1, comprising releasing bubbles of the gas phase from the distributor having a diameter of 5–10 mm.

13. The process according to claim 1, wherein the alkylbenzene contains at least one methyl group.

14. The process according to claim 1, wherein the alkylbenzene is toluene.

15. The process according to claim 1, wherein the gas phase comprises chlorine.

16. The process according to claim 1, wherein the liquid phase comprises toluene and the gas phase comprises chlorine.

17. A process for halogenating alkylbenzenes in an axially symmetrical photochemical gas/liquid reactor, wherein said reactor comprises:

a vessel;

a central radiation source;

at least one gas distributor at the bottom of said reactor; and an inner sleeve means arranged concentrically between the radiation source and the vessel, said inner sleeve means allowing internal recirculation of reaction liquid, said recirculation comprising a rising movement of the liquid in the space situated between the radiation source and the inner sleeve means and a descending movement in the space situated between the vessel and the inner sleeve means, said process comprising:

introducing a liquid phase comprising an alkylbenzene into the vessel and a gas phase comprising a halogen into the gas distributor;

providing the liquid rising in the space situated between the radiation source and the inner sleeve means with a velocity of 0.1–0.8 m/s;

occupying 10–50% of a volume defined between the radiation source and the inner sleeve means with the gas phase;

releasing bubbles of the gas phase from the distributor having a diameter of 3–15 mm; and recirculating the reaction liquid within the vessel;

whereby a reaction product is formed which is substantially free of derivatives of alkylbenzene that are halogenated on the aromatic ring.

* * * * *